United States Patent
Day et al.

(10) Patent No.: US 6,817,222 B2
(45) Date of Patent: Nov. 16, 2004

(54) METHOD, APPARATUS AND SYSTEM FOR ASSESSING HAIR CONDITION

(75) Inventors: Shane Alistair Day, Warwick (GB); Linda Helen Jacobs, Thatcham (GB); Ke Ming Quan, West Chester, OH (US); Tracy Stephens, Warfield (GB); Robert Woolston, Moreton Morrell (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/396,974

(22) Filed: Mar. 25, 2003

(65) Prior Publication Data

US 2003/0233861 A1 Dec. 25, 2003

Related U.S. Application Data

(63) Continuation of application No. PCT/US01/42265, filed on Sep. 24, 2001.

(51) Int. Cl.$^7$ ................................................. G01N 3/56
(52) U.S. Cl. ........................................................... 73/9
(58) Field of Search ................................ 73/9, 86, 763, 73/159, 160

(56) References Cited

U.S. PATENT DOCUMENTS 3,676,769 A * 7/1972 Loepfe ........................ 324/454
4,917,647 A * 4/1990 Wetherell et al. ............ 446/297
6,707,929 B2 * 3/2004 Marapane et al. .......... 382/100

FOREIGN PATENT DOCUMENTS

| | | |
|---|---|---|
| DE | 2719482 A | 11/1978 |
| EP | 0965834 A | 12/1999 |
| JP | 57017860 | 1/1982 |
| JP | 62273433 | 11/1987 |
| JP | 63163143 | 7/1988 |
| JP | 05256631 | 10/1993 |

* cited by examiner

*Primary Examiner*—Max Noori
(74) *Attorney, Agent, or Firm*—Brian M. Bolam; Marianne Dressman; Tara M. Rosnell

(57) ABSTRACT

Method for measuring friction in a hair sample, comprising: (a) providing a friction member; (b) drawing it through the hair, generating a frictional noise signal; and (c) capturing the signal by a noise sensor. Device suitable for use in said method, comprising comb means having a plurality of tines and a noise sensor arranged to capture frictional noise generated by passage of comb means through the hair. System for assessing the level of damage in a hair sample, comprising: (a) defining hair categories; (b) associating with each category a standard trace representative of the frictional noise signal generated when a standard sample in that category is subjected to said method; (c) assigning the sample to one of the categories; (d) carrying out said method on the sample; (e) visually displaying the frictional noise signal generated as a trace; (f) and comparing the sample's trace with the standard trace associated with the category.

16 Claims, 8 Drawing Sheets

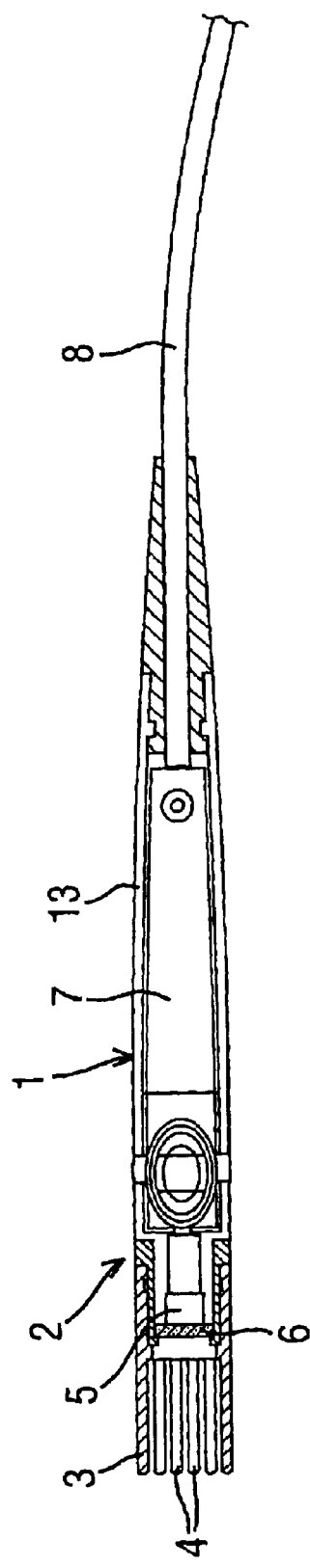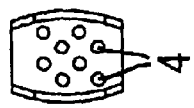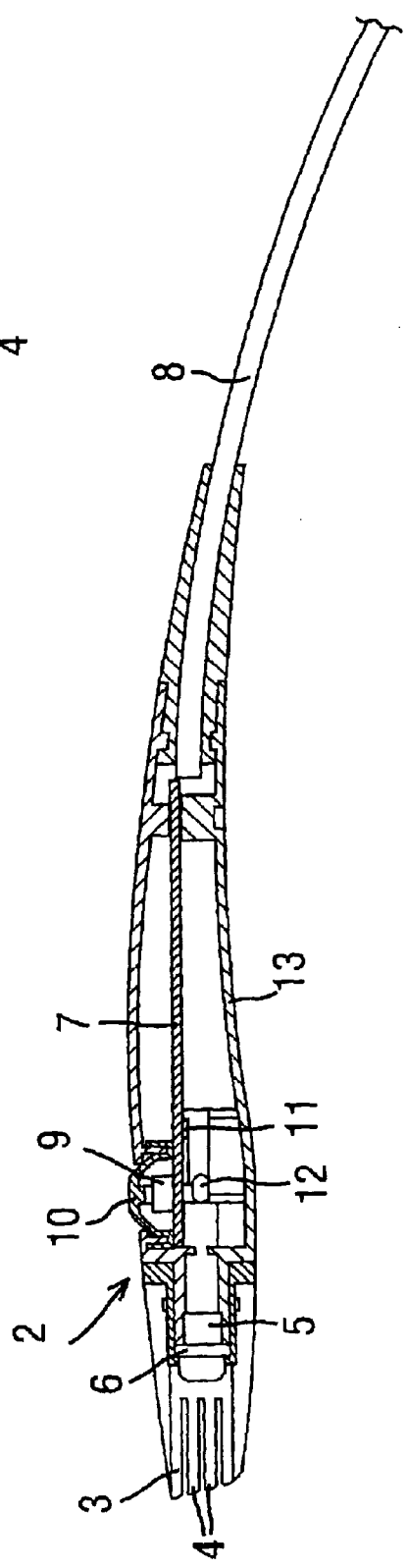

METHOD, APPARATUS AND SYSTEM FOR ASSESSING HAIR CONDITION

CROSS REFERENCE TO RELATED APPLICATION

The application is a continuation of International application PCT/US01/42265 (Case CM2437M) filed on Sep. 24, 2001.

TECHNICAL FIELD

This invention relates to an apparatus, a method and a system for assessing the condition of hair, in particular assessing the degree of damage in the hair.

BACKGROUND

In the hair care field it is often important to assess the condition of a consumer's hair. In particular it is often valuable to be able to assess the degree of damage sustained by the hair. It is known that the surface of a hair fibre becomes rougher when the hair is subjected to damage, for instance as a result of brushing, bleaching, perming, colouring, etc. This reduction in smoothness is believed to result from changes in the structure of the cuticle, the outermost part of the hair fibre.

It is known to assess roughness, and by implication damage by measuring the degree of friction generated by subjecting the hair to certain conditions. For instance, ease of combing is commonly used as a measure of smoothness. In one combing test the force required to detangle, by drawing a comb through, a bundle of hair fibres is used to assess friction, roughness and damage.

EP-A-965,834 describes friction-measuring equipment for evaluating the effects of cosmetics on skin, hair, membranes and eyes. This equipment assesses friction by means of deformation of a deformable assembly on a probe.

JP 63/163143 measures the degree of damage to hair by comparing forward and reverse friction forces. These forces are measured by means of a torque meter.

JP 62/273433 measures friction between hairs by passing a fluid in turbulent flow over a bundle of hair and measuring friction by detecting pressure loss in the fluid.

It would be desirable to be able to provide systems that allow the convenient measurement and analysis of surface friction of hair. It would also be desirable to provide a means of relating this to levels of damage across a range of hair types.

BRIEF DESCRIPTION OF THE DRAWINGS

The invention will now be illustrated with reference to the Figures, which show the following.

FIG. 1 is a top cross-sectional view of a preferred device according to the invention.

FIG. 2 is an end view of the same device.

FIG. 3 is a side cross-sectional view of the same device.

DETAILED DESCRIPTION OF THE INVENTION

A Method

Figure 4:
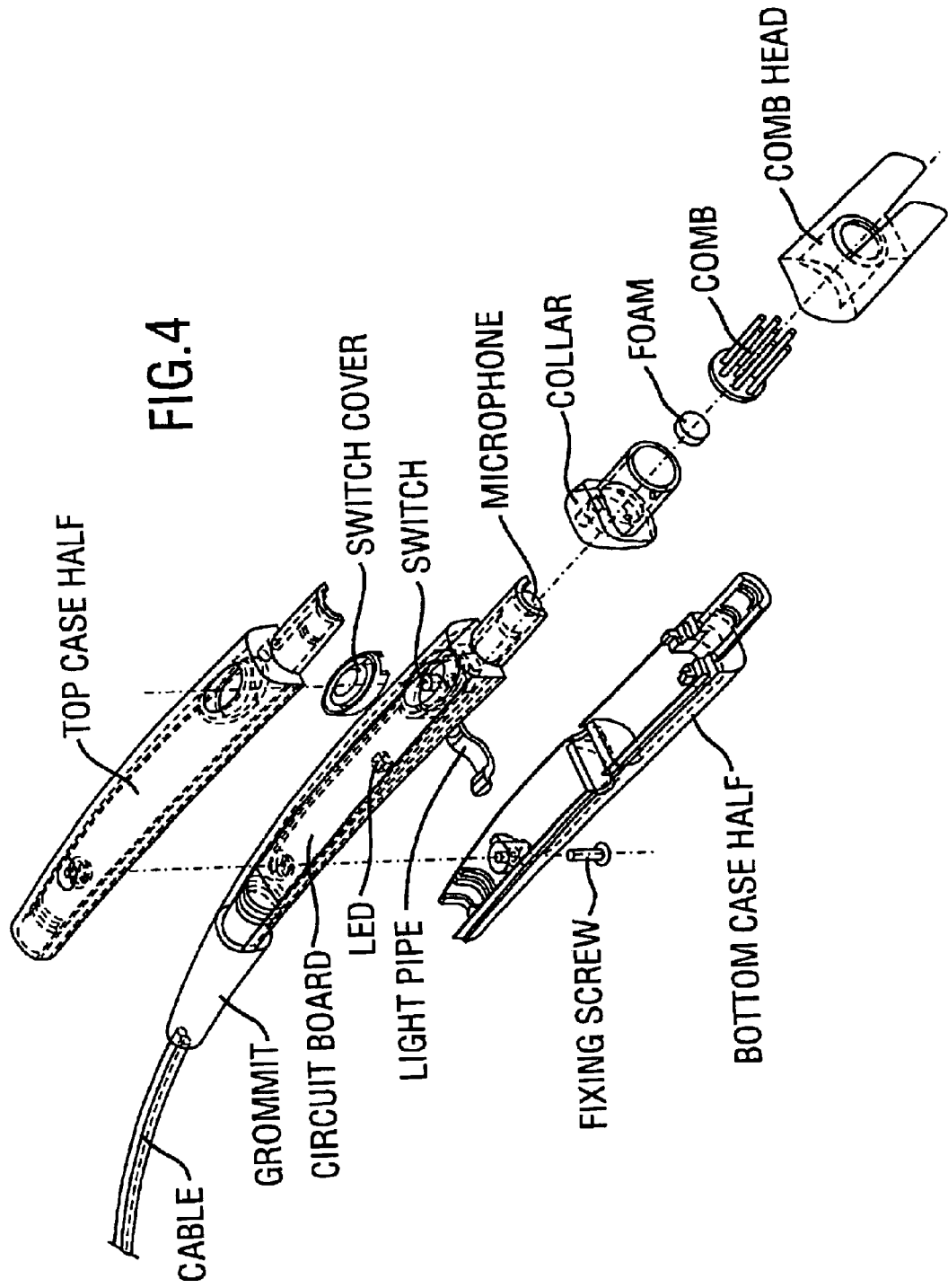
FIG. 4 is an exploded view of the same device.

According to a first aspect of the invention we provide a method for measuring the friction generated by a bundle of hair fibres, comprising providing a friction member, drawing the friction member through the bundle of hair, whereby a frictional noise signal is generated, and capturing the frictional noise signal by a noise sensor. Generally the captured noise signal is converted to a form that can be displayed. The converted signal is then displayed using display means. Such means may include, but is not limited to display screens selected from the group consisting of a computer screen, a cathode ray tube device, and a liquid crystal display device.

In the invention the friction generated by a bundle of hair is measured. The hair may be that of any mammal, preferably human, dog, horse, or cat, more preferably human hair. The bundle of hair may be a hair sample or switch but is preferably hair growing on the head of a consumer.

In the method it is necessary to use both a friction member and a noise sensor. The friction member is drawn through the bundle of hair such that it contacts and passes over the surfaces of the individual hairs. This creates friction between the friction member and the hairs. We find that the frictional noise generated depends upon the level of friction between the friction member and the hair surfaces.

The friction member is generally formed from rigid material, preferably polymeric material. For instance it may be formed from high-density polyethylene (HDPE).

The friction member is preferably in the form of a comb means having a plurality, preferably at least three, and more preferably at least four tines. The comb means is usually drawn through the bundle of hair in the manner usual for a comb. This may be done the subject whose hair is being assessed or by another.

The frictional noise signal generated is captured by means of a frictional noise sensor, preferably a microphone. The microphone may for instance be a standard electronic microphone or a noise-cancelling microphone.

Once the frictional noise has been captured it can be displayed and analysed in any suitable manner. Preferably a visual display unit is also provided and the frictional noise sensed by the sensor is converted to a signal that is then transferred to the visual display unit and displayed. It may for instance be displayed in the form of a trace of sound amplitude versus time. This conversion may be achieved using known means.

Preferably the display of the signal is substantially instantaneous, such that the frictional noise being generated by drawing the friction member through the bundle of hair is displayed at the same time as the friction member is being drawn through the bundle of hair.

In the method the frictional noise signal displayed may be obtained from a single pass of the friction member through the bundle of hair. Alternatively, the friction member may be drawn through the hair two or more times. Results may be accumulated or averaged.

While the inventive method provided herein may adequately be performed alone, it may further be performed in combination with other methods for assessing hair damage. Such additional methods to combined with the method herein may include, but are not limited to: intuitive-self-assessment by the subject, visual or physical assessment by the subject or another, such as a beauty counselor, assessment using other devices which measures hair damage, chemical assessment of the hair, e.g. assessing the amount of broken versus unbroken disulfide bonds of cysteine in a subject's hair, and combinations thereof. Suitable hair damage measuring methods for use herein include, but are not limited to methods that employ devices that assess roughness, and by implication damage by measuring the degree of friction generated by subjecting the hair to certain conditions. For instance, ease of combing is commonly used as a measure of smoothness. In one combing test the force required to detangle, by drawing a comb through, a bundle of hair fibres is used to assess friction, roughness and damage.

A Device

The invention also provides, in a second aspect, a device suitable for use in the method of the first aspect. The device comprises a comb means having a plurality of tines and a frictional noise sensor. The device as a whole is preferably designed so that it is suitable for use in the hand. It is often elongate. The comb means is generally placed at one end of an elongate device.

Preferably the device is provided in at least two separable parts. In this case the first part comprises the comb means and the second part comprises a housing that contains the frictional noise sensor and, if required, means for converting the signal detected by the frictional noise sensor to a signal transferable to a visual display unit.

The noise sensor should be close to the comb means to achieve optimum sensitivity to frictional noise generated. However, generally it should not be in contact with the comb means. Thus protection means are generally provided between the noise sensor and the comb means to prevent contact of the two components. This may be made from any material that is protective and acts to prevent contact between the comb means and noise sensor whilst allowing the passage of the frictional noise signal generated by contact of the comb means with hair.

For the purposes of detecting the frictional noise signal generated by comb means and hair we find that detection of frequencies in the range from about 50 Hz to about 5 kHz is preferred.

A device according the invention is exemplified in FIGS. 1 to 4. The device 1 is shown as elongate in shape. It has at its free end 2 a comb means 3 having tines 4. The comb may be formed from HDPE. The device 1 may be stored before and in between and after uses, e.g., on a magnetic stand.

The passage of the tines through a sample of hair generates frictional noise that is detected by the microphone 5. Between the microphone 5 and the comb is protective means 6 formed from foam, preferably open celled foam. The microphone 5 is connected to a circuit board 7, which converts the frictional noise generated to an electrical signal that passes along the cable 8 to means (not shown) for converting the signal into a visual display. For ease of use, the cable 8 may be situated as retractable.

The device 1 is constructed such that the microphone 5 detects signals at all times. The switch 9 can be switched by pressing the switch cover 10 to indicate that display and/or recording of the frictional noise signal should occur. The recording is indicated by an "on/off" LED, whose signal is visible from the exterior by means of the light pipe 12.

The microphone and circuit board are contained in a protective housing 13 that is removeably connected with the comb 3. The comb 3 may be removed for instance by twisting. This has the advantage that the comb may be removed for cleaning and replaced with a new comb.

Although it is known that there is a relationship between friction generated by combing hair and damage to that hair we have found that this is not the only significant factor when frictional noise is, as in the invention, used to assess friction levels. Frictional noise generation gives an accurate indication of friction levels but we have found that it is important to determine the characteristics of the hair being tested in order to assess whether the increased friction is due to damage and/or a rough hair surface or to other factors (for example hair curliness). We have found that this allows any particular hair sample (e.g. the hair of an individual consumer) to be analysed accurately for the level of damage in that particular hair sample. In the invention, varying friction and damage levels within a single sample may be observed by means of changes in amplitude as the comb means is passed through the sample.

A System

Thus according to a third aspect of the invention we provide a system for assessing the level of damage in a test sample of hair, comprising defining a predetermined number of hair categories H, associating with each hair category H a standard trace T representative of the frictional noise signal generated when a standard sample in that hair category is subjected to the method described above, assigning the test hair sample to one of the predetermined categories Ht, carrying out the method described above on the sample of hair, visually displaying the frictional noise signal generated as a trace on a screen, and comparing the sample's trace Tt with the standard trace T associated with the category Ht.

In this system it is necessary to define a number of predetermined categories of hair. These categories are defined by their tendency to give friction. For instance, in one system, three categories: high friction, moderate friction and low friction could be predetermined.

Hair of various types is then assigned to one of these predetermined categories according to relevant factors. These factors may be selected from ethnic origin (for instance if the hair is of European, Asian or African origin); waviness (whether the hair is straight, wavy or curly); whether the hair has been previously subjected to treatments (perming, bleaching or colouring). Thus this aspect of the invention is based at least in part on the realisation that frictional noise levels depend not only upon damage levels but on other hair characteristics.

With each category is associated a standard trace. This trace is an illustration of the frictional noise expected to be generated by a sample of hair in the defined category when subjected to the method described above.

In the system of the invention the hair sample to be tested, which may be a hair switch but is generally hair growing on the head of a consumer, is assigned to one of the predefined categories according to the factors discussed above.

The process of the invention is then carried out on the sample to be tested, generally in substantially the same manner as carried out to generate the standard traces above. The frictional noise signal generated is displayed as a trace on a screen and this sample trace is compared with the standard trace. It can then be assessed whether the hair sample is more or less damaged than would be expected from the characteristics above.

A significant factor is the amplitude of the frictional noise generated. In particular, when the trace is presented as a graph of the relationship between amplitude and time then the area under the curve is generally proportional to the level of friction.

Thus this system has the advantage that the level of damage in any particular hair sample can be accurately assessed whilst taking into account the level of friction to be expected as a result of its characteristics. For instance, virgin (untreated) straight hair naturally gives a lower level of frictional noise than virgin curly hair. Thus in order to assess the necessity for use of treatment products on the hair it is important to predetermine the natural level of frictional noise which would be expected for hair of the relevant category.

Figure 5:
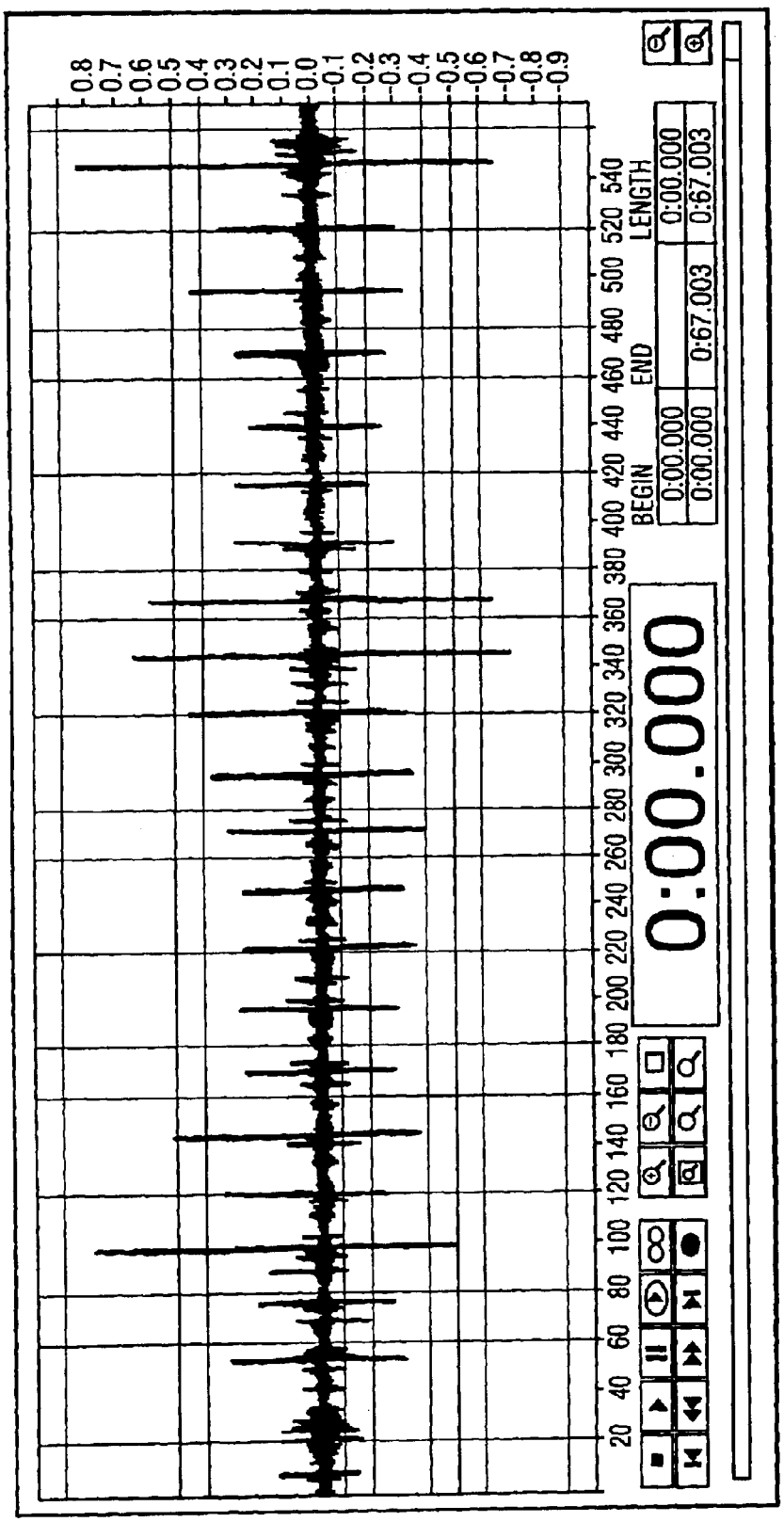
FIGS. 5 to 10 show example traces from six different categories of hair.
Figure 6:
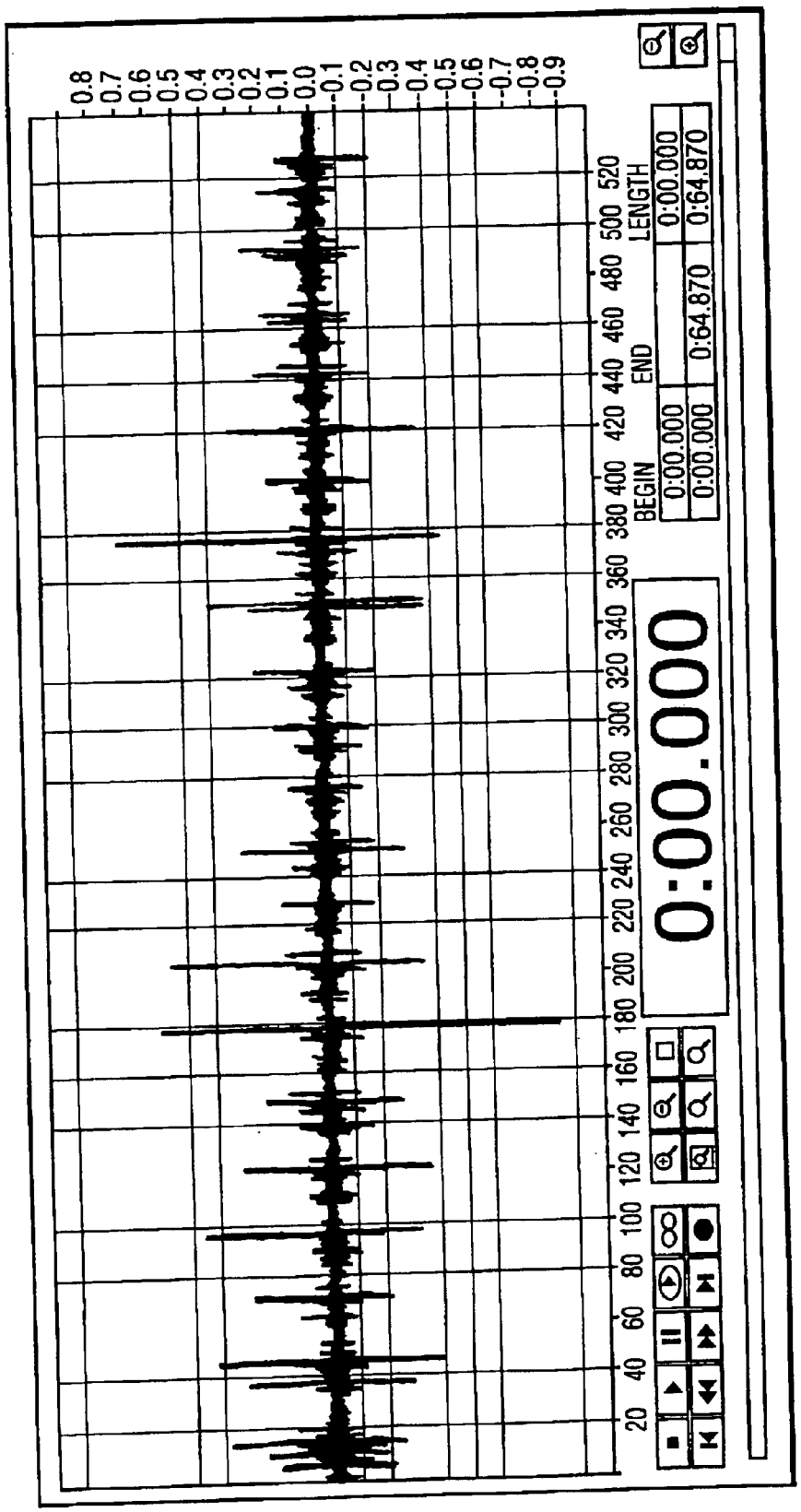
Figure 7:
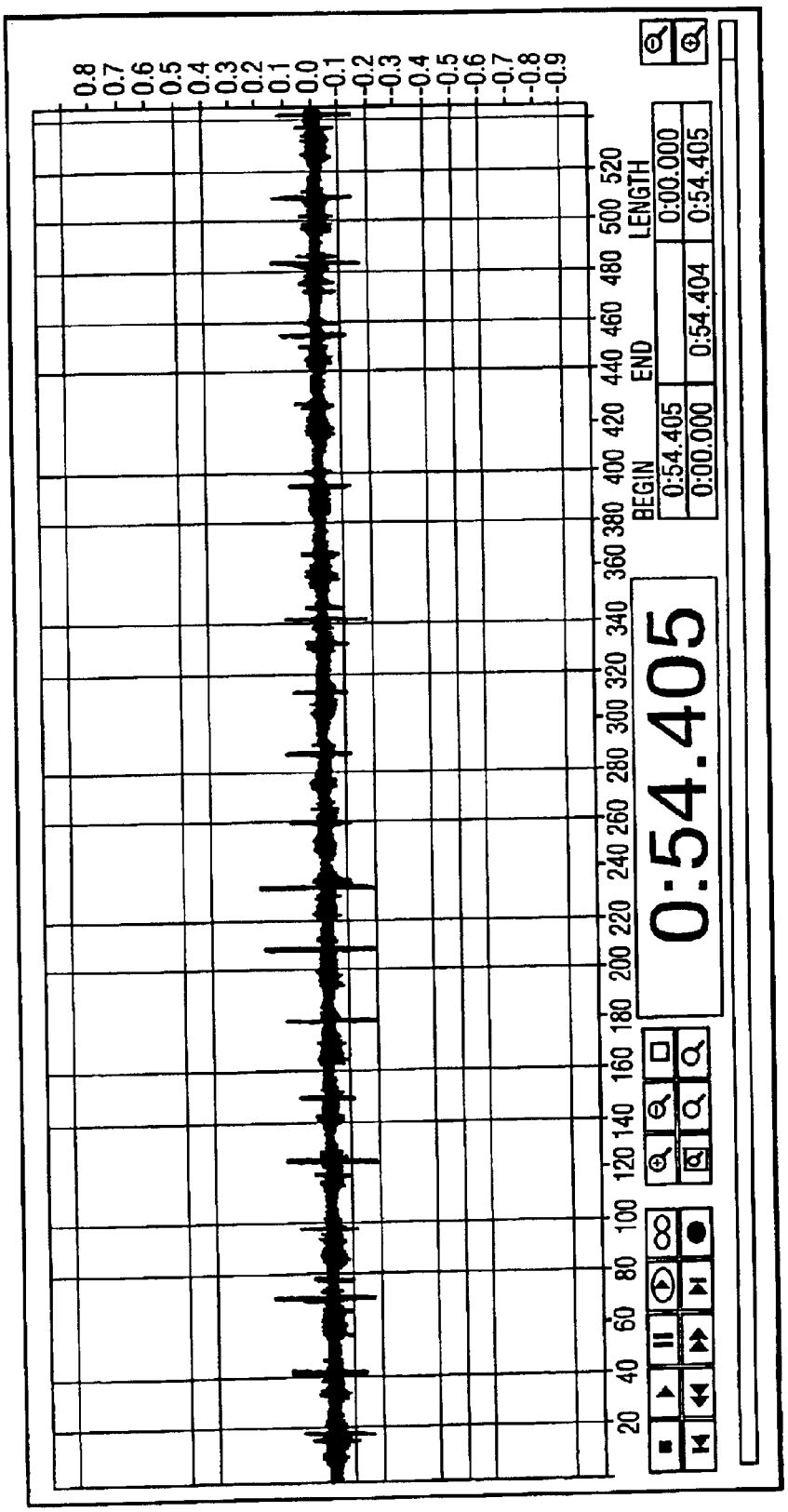
Figure 8:
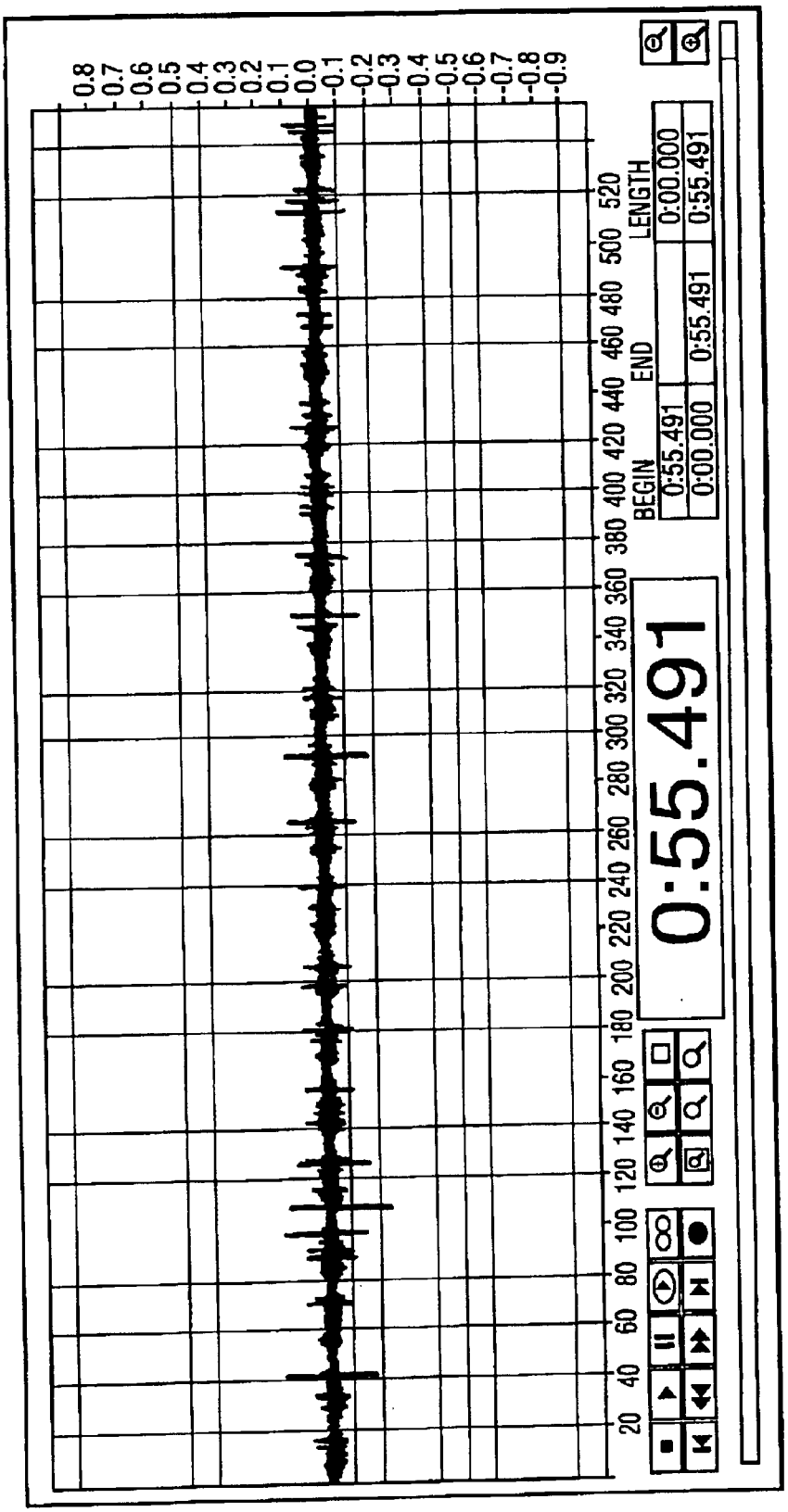
Figure 9:
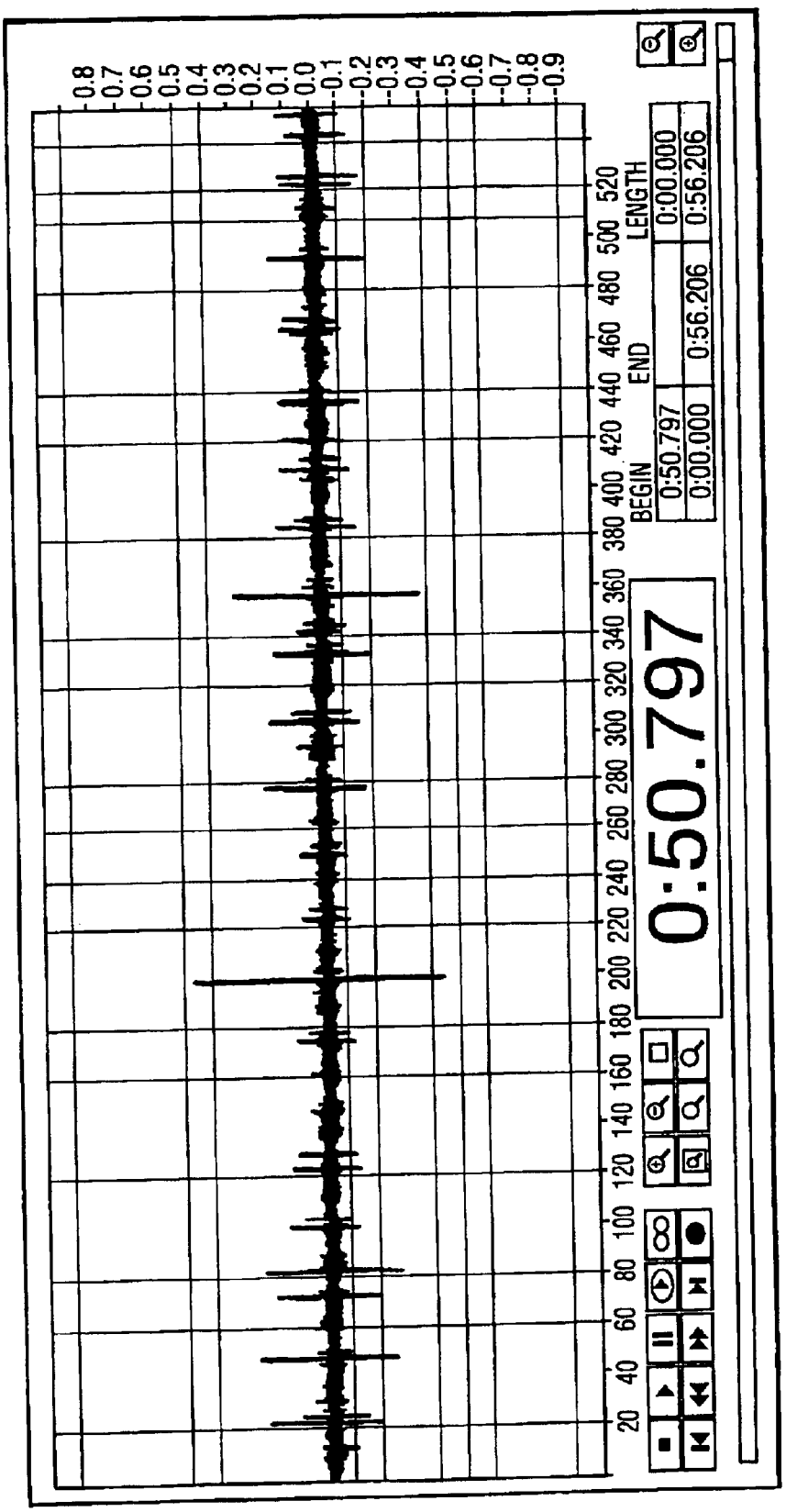
Figure 10:
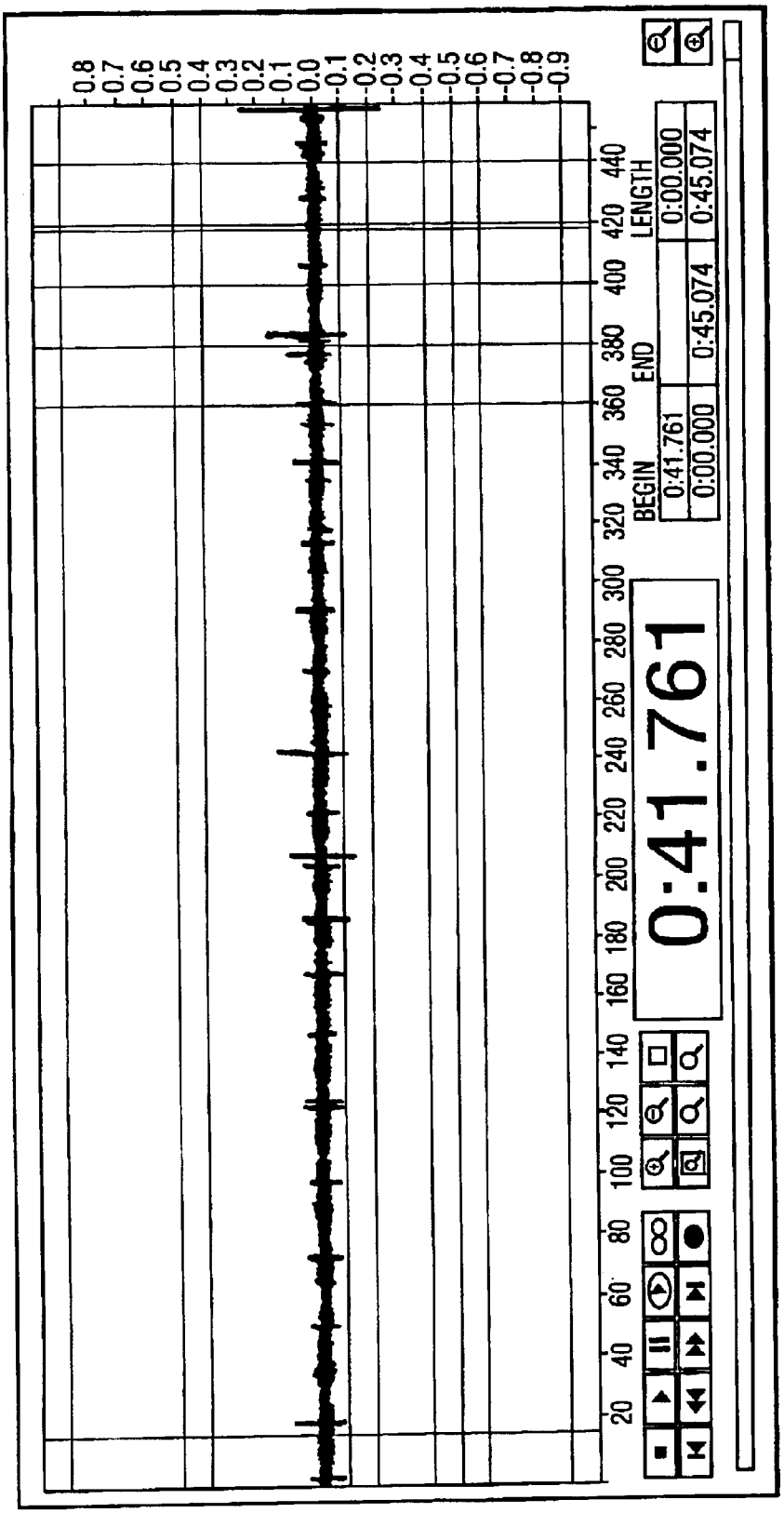

For example, the hair categories illustrated in FIGS. 5 to 10 may be used as the predefined categories and the traces used as the standard traces in a method according to the invention. FIG. 5 shows a standard trace for grey permed European hair. FIG. 6 shows a standard trace for brown curly European hair. FIG. 7 shows a standard trace for brown Asian hair. FIG. 8 shows a standard trace for grey hair. FIG. 9 shows a standard trace for brown permed and bleached European hair. FIG. 10 shows a standard trace for brown virgin European hair. The level of friction decreases from FIG. 5 to FIG. 10. This is proportional to the area under the trace and, generally, the amplitude of the trace.

The system can be used by the consumer directly but is preferably applied by an operative or adviser, for instance in a store or salon. It is contemplated that after the assessment has been made appropriate treatment for the hair may further be proposed.

What is claimed is:

1. A method for measuring friction in a bundle of hair, said method comprising the steps of:
    (1) providing a friction member;
    (2) drawing the friction member through the bundle of hair, whereby a frictional noise signal is generated; and
    (3) capturing the frictional noise signal by a noise sensor, wherein said noise detector detects sound.

2. A method according to claim 1, wherein the bundle of hair is that of a mammalian subject.

3. A method according to claim 1, further comprising visually displaying the frictional noise signal via display means.

4. A method according to claim 3 in which the frictional noise signal is displayed in the form of a trace showing variation of sound amplitude with time.

5. A method according to claim 3, wherein capturing the frictional noise signal by a noise sensor and visually displaying of the frictional noise signal occur simultaneously.

6. A method according to claim 1 further comprising using the generated frictional noise signal to assess degree of damage of the hair.

7. A method according to claim 1, wherein the noise sensor detects sound in a frequency range of about 50 Hz to about 5 kHz.

8. A device suitable for measuring friction in a bundle of hair, comprising a friction member which is a comb means having a plurality of tines and a frictional noise sensor arranged to capture frictional noise generated by passage of the comb means through the bundle of hair.

9. A device according to claim 8 in which the tines are formed from rigid polymeric material.

10. A device according to claim 8, which is formed from two portions that are removably attached, the first portion comprising the comb means and the second portion containing the frictional noise sensor.

11. A device according to claim 8 comprising protection means, positioned between the comb means and the frictional noise sensor, for preventing contact between the comb means and the frictional noise sensor.

12. A device according to claim 8, wherein the frictional noise sensor is a microphone.

13. A method for assessing the level of damage in a test sample of hair, said method comprising the steps of:
    a) defining a predetermined number of hair categories H;
    b) associating with each hair category H a standard trace T representative of the frictional noise signal generated when a standard sample in that hair category is subjected to the method of claim;
    c) assigning the test sample of hair to one of the predetermined categories Ht;
    d) carrying out the method of claim 1 on the test sample of hair, wherein a test sample trace Tt is generated;
    e) visually displaying the frictional noise signal generated as a trace on a display screen; and
    f) comparing the test sample trace Tt with the standard trace T associated with the category Ht.

14. A method according to claim 13 which comprises defining at least three different predetermined hair categories H each associated with a different standard trace T.

15. A method according to claim 13, wherein the assignment of the test sample of hair to one of the predetermined categories is carried out by taking into account any one or more of the following factors: ethnic origin, waviness and past hair treatments.

16. A method according to claim 13, wherein the test sample of hair is hair growing on the head of a test subject.

* * * * *